US008223982B2

(12) United States Patent
Ibrahim

(10) Patent No.: US 8,223,982 B2
(45) Date of Patent: Jul. 17, 2012

(54) AUDIO PATH DIAGNOSTICS

(75) Inventor: Ibrahim Ibrahim, North Ryde (AU)

(73) Assignee: Cochlear Limited, Macquarie University, NSW (AU)

( * ) Notice: Subject to any disclaimer, the term of this patent is extended or adjusted under 35 U.S.C. 154(b) by 1484 days.

(21) Appl. No.: 10/887,893

(22) Filed: Jul. 12, 2004

(65) Prior Publication Data

US 2005/0008177 A1    Jan. 13, 2005

(30) Foreign Application Priority Data

Jul. 11, 2003  (AU) ................................ 2003903576

(51) Int. Cl.
    *H04R 29/00*    (2006.01)
(52) U.S. Cl. ........................... 381/60; 381/312; 381/320
(58) Field of Classification Search ............... 381/56, 381/58, 1, 97, 98–103, 59–60, 312–331; 702/183; 600/559
    See application file for complete search history.

(56) References Cited

U.S. PATENT DOCUMENTS

| | | | | |
|---|---|---|---|---|
| 3,692,959 A | * | 9/1972 | Lamp ............................... | 381/60 |
| 3,784,750 A | * | 1/1974 | Stearns et al. .................. | 381/320 |
| 4,170,769 A | * | 10/1979 | Morris et al. ............... | 340/384.6 |
| 4,393,275 A | * | 7/1983 | Feldman et al. .............. | 381/320 |
| 4,410,970 A | * | 10/1983 | Law ............................ | 369/53.33 |
| 4,532,930 A | | 8/1985 | Crosby et al. | |
| 4,577,641 A | * | 3/1986 | Hochmair et al. ........... | 600/559 |
| 4,941,179 A | * | 7/1990 | Bergenstoff et al. ......... | 381/321 |
| 4,957,478 A | * | 9/1990 | Maniglia ........................ | 600/25 |
| 5,029,217 A | * | 7/1991 | Chabries et al. .............. | 381/317 |
| 5,061,282 A | * | 10/1991 | Jacobs ............................ | 623/10 |
| 5,303,306 A | * | 4/1994 | Brillhart et al. ............... | 381/315 |
| 5,583,969 A | | 12/1996 | Yoshizumi et al. | |
| 5,624,377 A | * | 4/1997 | Davis ............................. | 600/25 |
| 6,205,360 B1 | * | 3/2001 | Carter et al. .................... | 607/57 |
| 6,537,200 B2 | | 3/2003 | Leysieffer et al. | |
| 6,565,503 B2 | | 5/2003 | Leysieffer et al. | |
| 6,575,894 B2 | | 6/2003 | Leysieffer et al. | |
| 6,697,674 B2 | | 2/2004 | Leysieffer | |
| 6,876,750 B2 | * | 4/2005 | Allred et al. .................. | 381/314 |

(Continued)

FOREIGN PATENT DOCUMENTS

EP    0 788 290 A1    8/1997

(Continued)

OTHER PUBLICATIONS

Examiner's First Report dated Oct. 13, 2008, issued in connection with Australian Patent Application No. 2004203133.

(Continued)

*Primary Examiner* — Vivian Chin
*Assistant Examiner* — Fatimat O Olaniran
(74) *Attorney, Agent, or Firm* — Kilpatrick, Townsend & Stockton, LLP.

(57) ABSTRACT

In accordance with one aspect of the present invention, a method for detecting a change in the performance of an audio signal processing path is disclosed. The method comprises: selecting a characteristic of a received audio signal indicative of its energy content; determining first and second predetermined values of the selected energy characteristic at respective first and second audio signal frequency bands; calculating a ratio of the first and second predetermined values for a reference time period and a test time period; and comparing the ratio at the reference time period with the ratio of the test time period to determine a performance change in the audio path.

40 Claims, 4 Drawing Sheets

U.S. PATENT DOCUMENTS

| | | | |
|---|---|---|---|
| 7,013,011 B1 * | 3/2006 | Weeks et al. | 381/98 |
| 7,043,303 B1 * | 5/2006 | Overstreet | 607/57 |
| 2002/0048374 A1 * | 4/2002 | Soli et al. | 381/60 |
| 2004/0141621 A1 * | 7/2004 | Boonen et al. | 381/60 |

FOREIGN PATENT DOCUMENTS

| | | |
|---|---|---|
| EP | 1 276 349 A1 | 1/2003 |
| JP | 2000041300 A | 8/2000 |

OTHER PUBLICATIONS

English translation of a First Office Action dated Jan. 31, 2005, issued in connection with Austrian Official File No. 3A A 1177/2004-2.

* cited by examiner

AUDIO PATH DIAGNOSTICS

CROSS-REFERENCE TO RELATED APPLICATIONS

This application claims the priority of co-pending Australian Patent No. 2003903576, entitled "Audio Path Diagnostics," filed Jul. 11, 2003. The entire disclosure and contents of the above application is hereby incorporated by reference herein.

This application is related to U.S. Pat. Nos. 4,532,930, 6,537,200, 6,565,503, 6,575,894, and 6,697,674. The entire disclosure and contents of the above patents are hereby incorporated by reference herein.

BACKGROUND

1. Field of the Invention

The present invention relates generally to audio signal processing and, more particularly, to audio path diagnostics.

2. Related Art

The use of patient-worn and implantable medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as Cochlear™ prostheses, organ assist or replacement devices, and other medical devices, have been successful in performing life saving and/or lifestyle enhancement functions for a number of individuals.

One category of such medical devices are hearing prostheses which include but are not limited to hearing aids and Cochlear™ implant systems. Hearing aids are externally-worn devices which amplify sound to assist recipients who have degraded or impaired hearing due to, for example, age, injury or chronic ear or mastoid infections. Cochlear™ implant systems provide the benefit of hearing to individuals suffering from severe to profound hearing loss. Hearing loss in such individuals is due to the absence or destruction of the hair cells in the cochlea which transduce acoustic signals into nerve impulses. Cochlear™ implants essentially simulate the cochlear hair cells by directly delivering electrical stimulation to the auditory nerve fibers. This causes the brain to perceive a hearing sensation resembling the natural hearing sensation normally delivered to the auditory nerve.

Hearing prostheses usually involve the recipient having to wear various electronic components. The performance of such components, particularly those associated with the processing of audio sound, collectively and generally referred to as the audio path, can sometimes deteriorate in a very slow, almost undetectable fashion.

For example, hair and skin particles such as dandruff can settle near the port openings leading to the audio pickup devices such as microphones. These obstructing particles can adhere to the device due to the presence of natural body oils or other substances. Eventually accumulation of such particles may cause changes in the sound quality if left unchecked. There may be other reasons for gradual deterioration in the performance of the audio path, including those related to natural wear and tear as well as aging of mechanical and electro-acoustic parts.

This gradual deterioration in performance is particularly problematic when the recipient of the hearing prosthesis is a child or infant. Such recipients are often unable to report changes in hearing prosthesis functionality, particularly if the gradual drop in performance is related to speech intelligibility. This in turn can impact on the child's speech development and their learning and communication abilities.

SUMMARY

In accordance with one aspect of the present invention, a method for detecting a change in the performance of an audio signal-processing path is disclosed. The method comprises: selecting a characteristic of a received audio signal indicative of its energy content; determining first and second predetermined values of the selected energy characteristic at respective first and second audio signal frequency bands; calculating a ratio of the first and second predetermined values for a reference time period and a test time period; and comparing the ratio at the reference time period with the ratio of the test time period to determine a performance change in the audio path.

In accordance with another aspect of the present invention, an apparatus for detecting a change in the performance of an audio signal processing path is disclosed. The apparatus comprises: means for determining first and second predetermined values of a selected characteristic at respective first and second frequency bands of a received audio signal, wherein the selected characteristic is indicative of the energy content of the audio signal; means for calculating a ratio of the first and second predetermined values for a reference time period and a test time period; and means for comparing the ratio at the reference time period with the ratio of the test time period to determine a performance change in the audio path.

DETAILED DESCRIPTION

Embodiments of the present invention are described below in connection with one embodiment of an exemplary hearing prosthesis, a Cochlear™ prosthesis (also referred to as a Cochlear™ implant system, Cochlear™ prosthetic device and the like). Cochlear™ implant systems use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a Cochlear™ prosthetic device provides stimulation of the cochlear nucleus in the brainstem.

Figure 1:
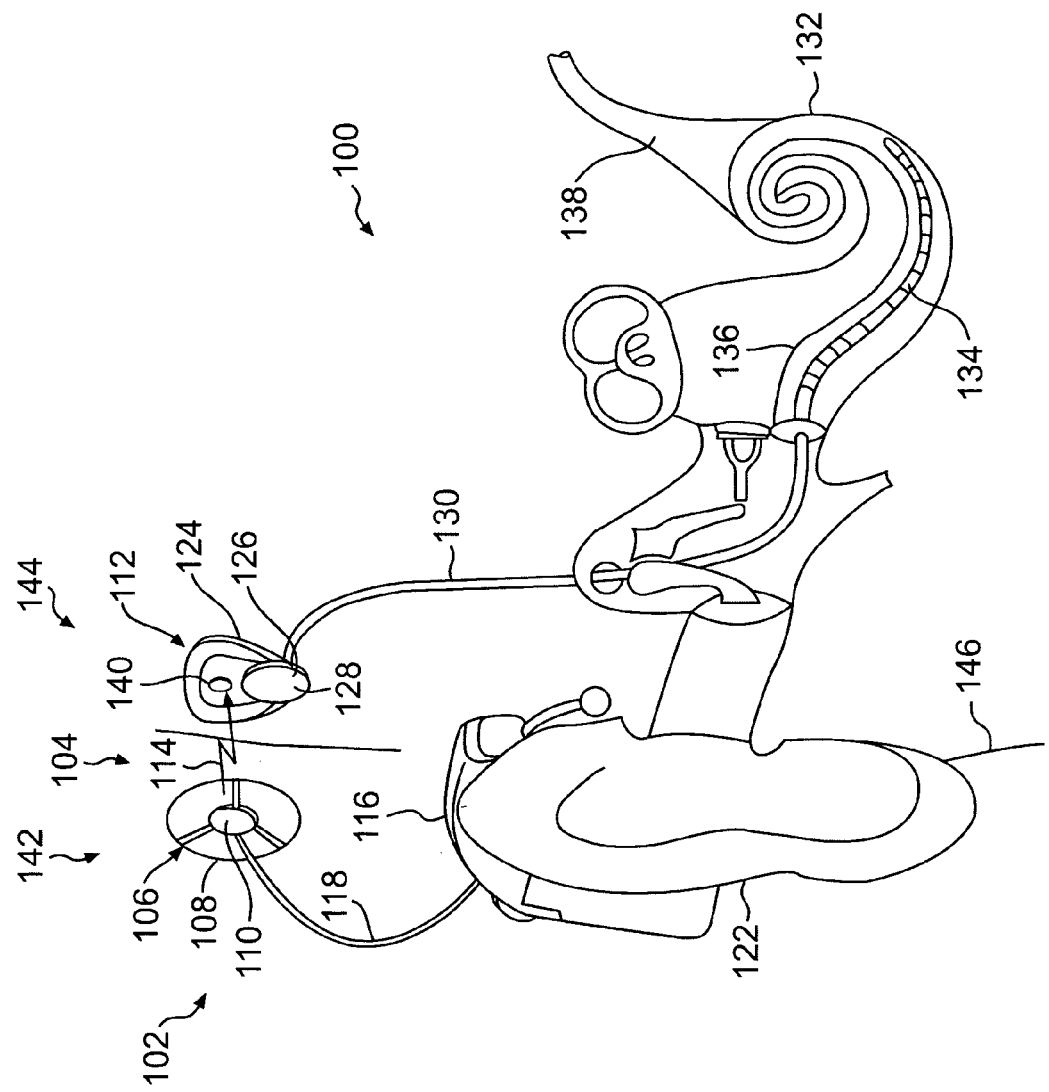
FIG. 1 is a simplified perspective view of internal and external components of an exemplary Cochlear™ implant system shown in their operational position on a recipient, in accordance with one embodiment of the present invention.

Exemplary Cochlear™ prostheses in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1 is a schematic diagram of an exemplary Cochlear™ implant system 100 in which embodiments of the present invention may be implemented Cochlear™ implant system 100 comprises external component assembly 142 which is directly or indirectly attached to the body of the recipient, and an internal component assembly 144 which is temporarily or permanently implanted in the recipient. External assembly 142 typically comprises audio pickup devices (not shown) for detecting sounds, a speech processing unit 116 that converts the detected sounds into a coded signal, a power source (not shown), and an external transmitter unit 106. External transmitter unit 106 comprises an external coil 108, and, preferably, a magnet 110 secured directly or indirectly to external coil 108. Speech processor 116 processes the output of the audio pickup devices that may be positioned, for example, by the ear 122 of the recipient. Speech processor 116 generates a stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to the basilar membrane 136 thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone moulding (not shown). In use, implantable receiver unit 112 may be positioned in a recess of the temporal bone adjacent ear 122 of the recipient.

Figure 2A:
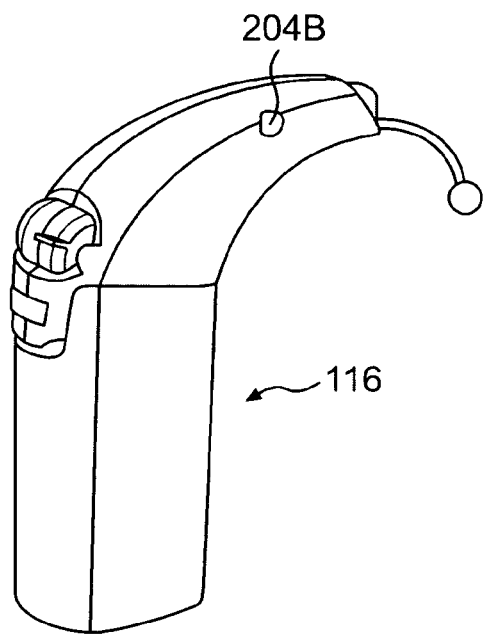
FIGS. 2A-2C are perspective views of an external speech processing unit used in the Cochlear™ implant system of FIG. 1, in accordance with one embodiment of the present invention.
Figure 2B:
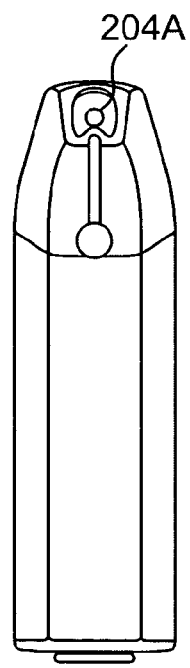
Figure 2C:
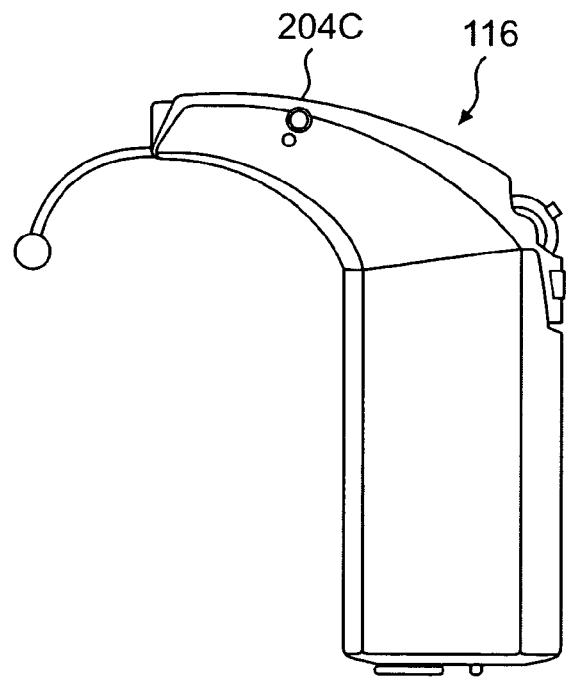

FIGS. 2A-2C are perspective views of an external speech processing unit 116 of Cochlear™ implant system 100, introduced above with reference to FIG. 1. Speech processor unit 116 has, as noted, a behind-the-ear configuration. External speech processing unit 116 includes at least one directional microphone (not visible) having a front port 204A and two rear ports 204B and 204C through which sound is received.

Speech processing unit 116 may experience a gradual, and at times undetectable, degradation of its ability to process sound due to the infiltration or accumulation of hair and skin particles in and through ports 204. Also, liquid in the form of sweat or humidity may accumulate in speech processing unit 116 to slowly deteriorate components and/or component connections within the unit. Finally, the ability to process audio signals may also be compromised by component wear due to extended use.

This gradual deterioration in performance can be particularly problematic when the recipient of the hearing prosthesis is a child or infant. Such recipients are often unable to report changes in the functioning, particularly if the gradual drop in performance is related to speech intelligibility. This in turn can impact on the child's speech development and their learning and communication abilities. The present invention is directed to a system and method for diagnosing degradations in the components which are involved in the processing of the audio signals, referred to herein as the audio signal processing path or simply, audio path.

Figure 3:
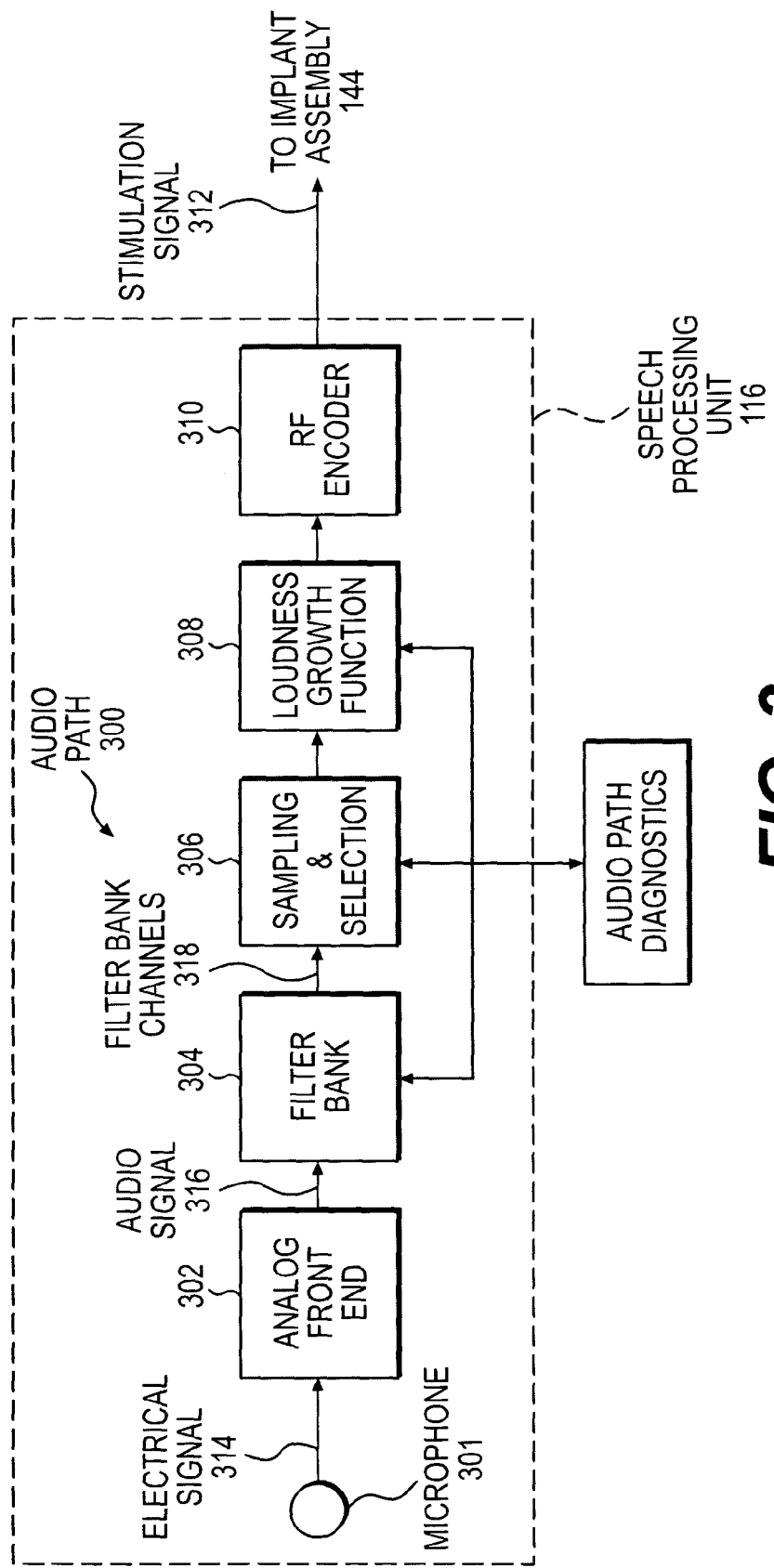
FIG. 3 is a functional block diagram of an audio signal processing path used in the Cochlear™ implant system of FIG. 1, in accordance with one embodiment of the present invention.

As noted, the components of a hearing prosthesis associated with the processing of audio sound are generally and collectively referred to herein as the audio path. FIG. 3 is a functional block diagram of one embodiment of an audio path 300 implemented in speech processor unit 116. Audio path 300 comprises a microphone or other audio pickup device, analog front end 302, a filter bank 304, a sampling and selection stage 306, a loudness growth function stage 308 and an RF encoder 310. The output of audio path 300 is a stimulation signal 312 which is transmitted to implanted assembly 144.

The audio pickup devices receive sound which is converted to an electrical signal 314. Electrical signal 314 is sent to analog front end 302, which is also known as an audio pre-processor. Generally, analog front end 302 amplifies electrical signal 314 received from microphone 301. In particular, analog front end 302 amplifies the higher frequency components of electrical signal 314 to overcome the natural concentration of energy in the lower frequencies. The structure and operation of analog front end 302 is considered to be well-known to those of ordinary skill in the art and, therefore, is not described further herein.

If desired, the gain of analog front end 302 can be adjusted through an external sensitivity controller (not shown). Further, analog front end 302 may also include an automatic gain and sensitivity controller, the operation of which is well-known in the art.

Analog front end 302 generates an audio signal 316 which is received by filter bank 304. Filter bank 304 comprises an array of band-pass filters (not shown) that process the input frequency range. As is well-known to those of ordinary skill in the art, the frequency bounds are based on critical bands, roughly linearly spaced below 1000 Hz and logarithmically spaced above 1000 Hz. It should be appreciated that other approaches now or later developed may also be utilized. Preferably, filter bank 304 is programmable since different speech coding strategies use different numbers of band-pass filters.

The output of each filter in filter bank 304, commonly referred to as a filter bank channel 318, is the envelope of the filtered audio signal 316 which is an estimate of the instantaneous power in the frequency range corresponding to the band of that filter. The structure and operation of filter bank 304 is considered to be well-known to those of ordinary skill in the art and, therefore, is not described further herein.

The output from each filter is then sampled at sampling & selection block 306, and the total energy in each frequency band is determined. The structure and operation of sampling & selection block 306 is also considered to be well-known to those of ordinary skill in the art.

Thereafter, at block 308 the acoustic or electric stimulation levels are determined according to the recipient's exact response pattern requirement. The individual response pattern data, includes threshold and comfort levels for each electrode in electrode array 134. This individual response data is stored in memory. The output signals from each channel 318 are digitized and modified by a microprocessor of loudness and growth function block 308 to reflect normal variations of hearing sensitivity with frequency. The structure and operation of loudness and growth function block 308 is considered to be well-known to those of ordinary skill in the art and, therefore, is not described further herein.

The output from some or all of these preset bands (depending on the strategy) is encoded at RF encoder block 310, and transmitted by external coil 106 (FIG. 1) to the internal components 144 of Cochlear™ implant 100.

As noted, audio path 300 can experience a gradual, and at times undetectable, degradation of its ability to process sound. The audio path diagnostic technique of the present invention detects changes in audio path performance. In particular, embodiments of the audio path diagnostic technique of the present invention detects gradual changes in performance which traditionally would not be detected until the Cochlear™ implant system fails or undergoes some periodic maintenance.

The audio diagnostic technique of the present invention detects a change in audio path performance based on changes in a ratio of a selected characteristic indicative of the energy contained in selected high and low frequency bands of the audio signal. Degradation of audio path performance has been observed to manifest itself in a deterioration of the ability of the audio path to process higher frequency portions of the audio spectrum. Thus, the ratio of the energy contained in selected high- and low-frequency bands will change when such degradation of audio path performance occurs. Advantageously, such a ratio is not affected by changes in the energy content of the audio signals due to volume adjustments made by the recipient, since such adjustments affect the entire frequency range of the audio signal.

The selected energy characteristic (EC) may be any characteristic indicative of the energy content of the audio signal. For example, in one embodiment, the selected energy characteristic is the voltage of the audio signal, while in an alternative embodiment the selected energy characteristic is the current of the audio signal. In addition, the selected energy characteristic may represent the maximum energy, average energy, etc. of the audio signal. Accordingly, the measured EC value may be the mean, median, root mean square (RMS), maximum or other measured or calculated value of the selected energy characteristic.

In operation, the selected energy characteristic is obtained from filter bank 304 for, as noted, a selected high-frequency channel and a selected low-frequency channel. A ratio of the selected characteristic is then formed, such that $$Q = (EC_{HF}/EC_{LF}),$$

where, $EC_{HF}$=value of the energy characteristic at the selected high-frequency band; and $EC_{LF}$=value of the selected energy characteristic at the selected low-frequency band.

As noted, audio path performance degradation is typically a gradual phenomenon. Thus, an immediate or short-term fall-off of performance cannot be relied upon as an indication of a degraded audio path. Rather, in accordance with one aspect of the invention, the change in the energy characteristic ratio, Q, is monitored. In one embodiment, a reference value, $Q_{REF}$, for performance ratio Q is obtained once or periodically for comparison with a current value $Q_{TEST}$, of performance ration Q. For example, the performance ratio Q may be periodically calculated over the course of a month, and then averaged or otherwise processed to derive a reference ratio value ($Q_{REF}$) which defines acceptable or normal audio path operations. The selected time intervals utilized to determine $Q_{REF}$ may be different for different hardware designs and settings.

The current performance ratio, $Q_{TEST}$, may be a single measurement taken periodically. In one alternative embodiment, $Q_{TEST}$ is determined once during an immediately preceding short term period of time, for example, a single day. If more than one value is determined, the values are then averaged or otherwise numerically combined to obtain a single value, $Q_{TEST}$, for comparison with $Q_{REF}$.

A performance factor is then periodically calculated, using the formula:

$$K = (Q_{TEST}/Q_{REF}),$$

where, $Q_{TEST}$=value of the performance ratio determined at a test time period; and $Q_{REF}$=value of the performance ratio determined at a referenced time period.

The performance factor K is desirably calculated on a regular basis, for example, every 24 hours, although other suitable intervals could be used.

When the value of performance factor K is approximately one (1), then $Q_{TEST}$ is approximately equal to $Q_{REF}$. However, as $Q_{TEST}$ diverges from $Q_{REF}$ over time, then such divergence is reflected in a change performance factor K. Such changes in performance factor K may be used to notify the recipient, and/or the carers, of a potential degradation of audio path performance. As one of ordinary skill in the art would appreciate, the degree of divergence which would be considered sufficient to generate such notification may vary according to the characteristics of the audio path. For example, in one embodiment, performance factor K must change by at least 10% for a period of three days for a notification to be broadcast.

As one of ordinary skill in the art would appreciate, any technique for notifying the recipient may be used. For example, a visible and/or audible alarm or indicator may be activated to notify the recipient that audio path 300 is not performing as desired. A person responsible for the operation of the prosthesis can then have Cochlear™ implant 100 serviced to restore the specified performance levels.

Figure 4:
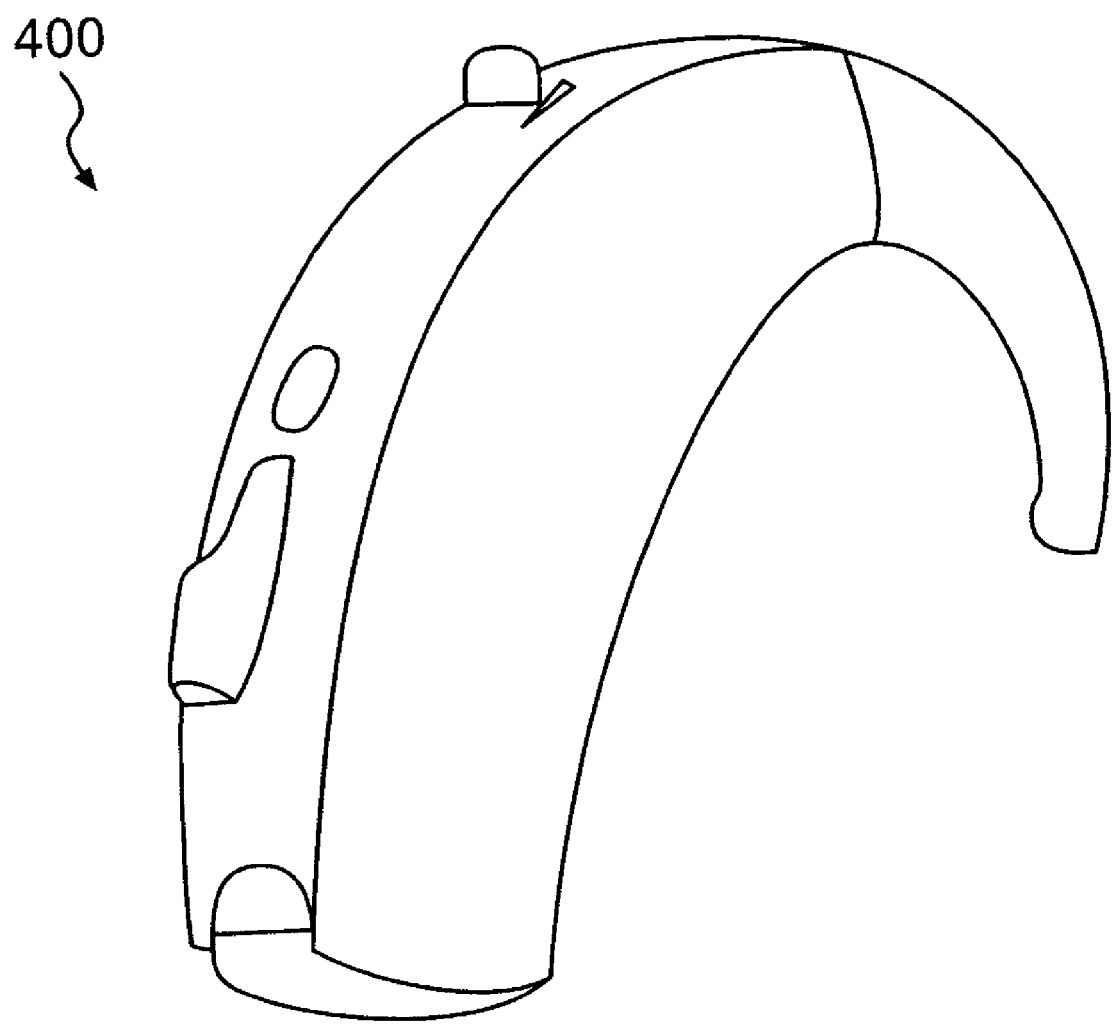
FIG. 4 is a perspective view of a conductive hearing aid, in accordance with one embodiment of the present invention.

The method of detecting a change in performance as described herein can alternatively be applied to the audio path of a conductive hearing aid. An example of such a hearing aid 400 is shown in FIG. 4. Here, the implemented audio path may comprise, for example, the microphone that receives an acoustic input signal and converts it into an electrical signal, a filter which processes the signal; an amplifier which produces an amplified output signal therefrom; and an output converter.

It will be appreciated by persons skilled in the art that numerous variations and/or modifications may be made to the invention as shown in specific embodiments without departing from the spirit or scope of the invention as broadly described. For example, the audio path diagnostic techniques of the present invention have been presented in the context of hearing prosthesis such as Cochlear™ implant system 100 and conductive hearing aid 400. It should be appreciated that the audio path diagnostic techniques of the present invention can be applied to other devices implementing an audio signal processing path. As another example, the above embodiments are described in the context of a particular audio pickup device, a microphone. It should be appreciated, however, that the present invention can be used in connection with audio paths implementing other types of audio pickup devices now or later developed. Furthermore, such audio pickup devices may not be positioned in locations described above. As a further example, it should be appreciated that the teachings of the present invention can be used not only to determine degradation of an audio path but also the performance of an audio path when reconfigured. For example, the performance of the audio path implemented in Cochlear™ implant system 100 above may be different if the type, size, quantity or location of the audio pickup device is changed. The audio path diagnostic techniques of the present invention can implemented to determine if such changes result in an increase or decrease in the performance of the implemented audio path. As a further example, in the above-embodiment the energy content of the high-frequency and low-frequency bands of the audio spectrum were determined and processed as described above. However, other cause of performance degradation may adversely affect certain frequency bands as compared with others. If detection of such causes are desired then the energy characteristic ratio may be obtained for other frequency bands rather then the high- and low-frequency bands noted above. The present embodiments are, therefore, to be considered in all respects as illustrative and not restrictive.

What is claimed is:

1. A method for detecting a change in performance of a hearing prosthesis comprising an audio signal processing path, the method comprising:
   receiving sound;
   converting the received sound into an audio signal;
   determining, by the hearing prosthesis, first and second reference values of a selected characteristic of the audio signal at first and second frequency bands of the audio signal, respectively, during a reference time period, wherein the selected characteristic is indicative of the energy content of the audio signal;
   determining, by the hearing prosthesis, first and second test values of the selected characteristic of the audio signal at the first and second frequency bands, respectively, during a test time period;
   calculating a reference ratio based on a ratio of the first and second reference values;
   calculating a test ratio based on a ratio of the first and second test values; and
   determining whether degradation has occurred over time in the audio signal processing path of the hearing prosthesis based on a comparison of the reference ratio with the test ratio.

2. The method of claim 1, wherein the selected energy characteristic is at least one of voltage of the audio signal and current of the audio signal.

3. The method of claim 1, wherein the first and second reference values are maximum values of the selected energy characteristic at the first and second audio signal frequency bands, respectively.

4. The method of claim 1, wherein the first and second reference values are median values of the selected energy characteristic at the first and second audio signal frequency bands, respectively.

5. The method of claim 1, wherein the first and second reference values are root mean square (RMS) values of the selected energy characteristic at the first and second audio signal frequency bands, respectively.

6. The method of claim 1, wherein the first frequency band is a higher frequency band than the second frequency band.

7. The method of claim 1, wherein the first frequency band is a lower frequency band than the second frequency band.

8. The method of claim 1, wherein said determining whether degradation has occurred over time in the audio signal processing path based on a comparison of the reference ratio with the test ratio comprises:
   dividing the reference ratio by the test ratio to determine a performance factor;
   comparing the performance factor with a change threshold; and
   sounding an alarm when the performance factor exceeds the change threshold.

9. The method of claim 1, wherein the hearing prosthesis comprises a cochlear implant system.

10. The method of claim 1, wherein the hearing prosthesis comprises a conductive hearing aid.

11. The method of claim 1, wherein the reference time period is a month.

12. The method of claim 1, wherein the reference time period is a first month of service.

13. The method of claim 1, wherein the test time period comprises a current day.

14. An apparatus for detecting a change in performance of a hearing prosthesis comprising an audio signal processing path, the apparatus comprising:
   means for receiving sound;
   means for converting the received sound into an audio signal;
   means for determining first and second reference values of a selected characteristic of the audio signal at first and second frequency bands of the audio signal, respectively, during a reference time period, wherein the selected characteristic is indicative of an energy content of the audio signal;
   means for determining first and second test values of the selected characteristic at the first and second frequency bands, respectively, during a test time period;
   means for calculating a reference ratio based on a ratio of the first and second reference values;
   means for calculating a test ratio based on a ratio of the first and second test values; and
   means for determining whether degradation has occurred over time in said audio signal processing path based on a comparison of the reference ratio with the test ratio.

15. The apparatus of claim 14, wherein said selected energy characteristic is at least one of voltage of the audio signal and current of the audio signal.

16. The apparatus of claim 14, wherein said first and second reference values are maximum values of the selected energy characteristic at the first and second audio signal frequency bands, respectively.

17. The apparatus of claim 14, wherein the first and second reference values are median values of the selected energy characteristic at the first and second audio signal frequency bands, respectively.

18. The apparatus of claim 14, wherein the first and second reference values are root mean square (RMS) values of the selected energy characteristic at the first and second audio signal frequency bands, respectively.

19. The apparatus of claim 14, wherein the first frequency band is a higher frequency band than the second frequency band.

20. The apparatus of claim 14, wherein determining whether degradation has occurred over time in the audio signal processing path based on a comparison of the reference ratio with the test ratio comprises:
   dividing the reference ratio by the test ratio to determine a performance factor;
   comparing the performance factor with a change threshold; and
   sounding an alarm when the performance factor exceeds the change threshold.

21. The apparatus of claim 14, wherein the hearing prosthesis comprises a cochlear implant system.

22. The apparatus of claim 14, wherein the hearing prosthesis comprises a conductive hearing aid.

23. The apparatus of claim 14, wherein the reference time period is a month.

24. The apparatus of claim 14, wherein the reference time period is a first month of service.

25. The apparatus of claim 14, wherein the test time period comprises a current day.

26. A cochlear implant system comprising:
an audio signal processing path comprising at least portions of one or more components of the cochlear implant system; and
an apparatus for detecting degradation in the audio signal processing path, comprising:
means for receiving sound;
means for converting the received sound into an audio signal;
means for determining first and second reference values of a selected characteristic of the audio signal at first and second frequency bands of the audio signal, respectively, during a reference time period, wherein the selected characteristic is indicative of an energy content of the audio signal;
means for determining first and second test values of the selected characteristic at the first and second frequency bands, respectively, during a test time period;
means for calculating a reference ratio based on a ratio of the first and second reference values;
means for calculating a test ratio based on a ratio of the first and second test values; and
means for determining whether degradation has occurred over time in said audio signal processing path based on a comparison of the reference ratio with the test ratio.

27. The system of claim 26, wherein the selected energy characteristic is one or more of voltage of the audio signal and current of the audio signal.

28. The system of claim 26, wherein the first and second reference values are maximum values of the selected energy characteristic at the first and second audio signal frequency bands, respectively.

29. The system of claim 26, wherein the first and second reference values are median values of the selected energy characteristic at the first and second audio signal frequency bands, respectively.

30. The system of claim 26, wherein the first and second reference values are root mean square (RMS) values of the selected energy characteristic at the first and second audio signal frequency bands, respectively.

31. The system of claim 26, wherein the first frequency band is a relatively high frequency band.

32. The system of claim 26, wherein the first frequency band is a relatively low frequency band.

33. The system of claim 26, wherein determining whether degradation has occurred over time in the audio signal processing path based on a comparison of the reference ratio with the test ratio comprises:
dividing the reference ratio by the test ratio to determine a performance factor;
comparing the performance factor with a change threshold; and
sounding an alarm when the performance factor exceeds the change threshold.

34. The system of claim 26, wherein the reference time period is a month.

35. The system of claim 26, wherein the reference time period is a first month of service.

36. The method of claim 1, further comprising:
outputting an indication in response to determining that degradation has occurred over time in the audio signal processing path.

37. The method of claim 36, wherein said outputting an indication in response to determining that degradation has occurred over time in the audio signal processing path comprises:
illuminating a visible indicator in response to determining that degradation has occurred over time in the audio signal processing path.

38. The method of claim 1, wherein said determining whether degradation has occurred over time in the audio signal processing path of the hearing prosthesis based on a comparison of the reference ratio with the test ratio comprises:
automatically determining whether degradation has occurred over time in the audio signal processing path of the hearing prosthesis based on a comparison of the reference ratio with the test ratio.

39. The apparatus of claim 14, further comprising:
means for outputting an indication in response to determining that degradation has occurred over time in the audio signal processing path.

40. The system of claim 26, wherein the apparatus for detecting degradation in the audio signal processing path further comprises:
means for outputting an indication in response to determining that degradation has occurred over time in the audio signal processing path.

* * * * *